United States Patent [19]
Thompson et al.

[11] Patent Number: 5,706,087
[45] Date of Patent: Jan. 6, 1998

[54] ELECTROMAGNETIC BEAM DIRECTING MEANS-SAMPLE ANALYSIS SYSTEM STAGE, AND METHOD OF USE

[75] Inventors: Daniel W. Thompson; Darin W. Glenn; John A. Woollam, all of Lincoln, Nebr.

[73] Assignee: The Board of Regents of the University of Nebraska, Lincoln, Nebr.

[21] Appl. No.: 727,700

[22] Filed: Oct. 4, 1996

[51] Int. Cl.$^6$ .................................................. G01J 4/00
[52] U.S. Cl. .................................... 356/364; 356/369
[58] Field of Search .......................... 356/364, 366, 356/367, 369, 381, 382, 118, 114, 16, 152, 116, 117; 250/201.2, 201.6, 225; 350/286, 394

[56] References Cited

U.S. PATENT DOCUMENTS

| | | | |
|---|---|---|---|
| 3,740,151 | 6/1973 | Chaney et al. | 356/117 |
| 3,874,797 | 4/1975 | Kasai | 356/118 |
| 3,880,524 | 4/1975 | Dill et al. | 356/118 |
| 4,770,505 | 9/1988 | Okazaki | 350/377 |
| 4,801,798 | 1/1989 | Lange | 250/225 |
| 4,917,461 | 4/1990 | Goldstein | 350/286 |
| 5,042,951 | 8/1991 | Gold et al. | 356/369 |
| 5,166,752 | 11/1992 | Spanier et al. | 356/369 |
| 5,521,706 | 5/1996 | Green et al. | 356/369 |

*Primary Examiner*—Frank G. Font
*Assistant Examiner*—Michael P. Stafira
*Attorney, Agent, or Firm*—James D. Welch

[57] ABSTRACT

Disclosed is an electromagnetic beam directing means for use with sample analysis systems, such as reflectometers, ellipsometers and polarimeters and the like, use of which facilitates investigation of sample systems which are not mounted to a sample analysis system sample system supporting stage. The present invention eliminates the requirement of extensive sample analysis system component realignment when alternatingly performing analysis of sample systems mounted upon, and mounted other than upon, a sample analysis system sample system supporting stage.

11 Claims, 1 Drawing Sheet

ELECTROMAGNETIC BEAM DIRECTING MEANS-SAMPLE ANALYSIS SYSTEM STAGE, AND METHOD OF USE

TECHNICAL FIELD

The present invention relates to sample analysis systems such as reflectometers, ellipsometers and polarimeters, and more particularly is a system and method of use thereof for facilitating investigation of sample systems which can not be mounted to a sample analysis system sample system supporting stage, and which does not require extensive sample analysis system component realignment to allow such investigation.

BACKGROUND

Sample analysis systems, such as reflectometers, ellipsometers, polarimeters, for use in investigating physical and optical properties of sample systems, are well known. Such sample analysis systems are generally comprised of components such as a source of an electromagnetic beam, a sample system supporting stage for supporting a sample system to be investigated, and a detector. In use such sample analysis systems typically produce an electromagnetic beam, cause it to impinge upon a sample system present upon the supporting stage, whereat it interacts with said sample system. Said interaction typically effects changes in polarization state and/or intensity of said electromagnetic beam, and also causes said electromagnetic beam to be directed into said detector.

A problem in use of reflectometers, ellipsometers, polarimeters and functionally similar sample analysis systems, however, presents when a sample system is physically too large to be supported on a sample system supporting stage thereof, or when a sample system must be placed into a housing which is too large to be supported on a sample system supporting stage thereof. The latter situation can arise where large magnets, for instance, must be present near a sample system to allow investigation of magneto-optical effects.

What users of reflectometer, ellipsometer, polarimeter, and functionally similar sample analysis systems typically must do when encountering such a situation, is place the sample system to be investigated other than upon said sample system supporting stage and reconfigure the system. Such reconfiguration is necessary to cause an electromagnetic beam produced by said electromagnetic beam source to be directed into a present detector. This generally means a completely different relative geometrical arrangement of electromagnetic beam source, and detector must be effected, as compared to the case where a sample system being investigated is supported by a sample analysis system sample system supporting stage. It is to be understood that any such major geometrical reconfiguration of reflectometer, ellipsometer, polarimeter and the like sample analysis system components, generally means that an alignment procedure must be performed to enable acquisition of usable data.

Where a user wishes to alternatingly investigate sample systems present on, and not on, a sample analysis system supporting stage then, it should be appreciated that the requirement to repeatedly perform alignment procedures can constitute a nuisance.

With an eye to the present invention, a Search of Patents was conducted, with the result being that very little was found. A Patent to Kasai, U.S. Pat. No. 3,874,797 is disclosed, however, as it describes a system for directing an electromagnetic beam utilizing totally reflecting prisms. As well, a Patent to Lange, U.S. Pat. No. 4,801,798 is disclosed as it describes a system which utilizes electromagnetic beam directing reflective means in a system which causes an electromagnetic beam to impinge upon an investigated sample system at a angle very near to a perpendicular to a surface thereof.

It is also noted that the reference titled "ELLIPSOMETRY AND POLARIZED LIGHT", by Azzam and Bashara, North-Holland, 1977 is incorporated by reference into this Disclosure for the purpose of providing general information regarding sample analysis systems utilizing electromagnetic beams, and fundamentals of electromagnetic beams.

It should then be apparent that a system, and method of its use, which would allow a user of a sample analysis system such as a reflectometer, ellipsometer, polarimeter or a functionally similar system, to alternatingly investigate sample systems present on, and not on, a sample system supporting stage thereof, without requiring major system reconfiguration procedures be performed, would be of great utility. The present invention provides such a system and method of its use.

DISCLOSURE OF THE INVENTION

The present invention is substantially found in a combination of an electromagnetic beam directing means and a sample analysis system sample system supporting stage which is typically utilized to support a sample system in said sample analysis system. It is noted that a preferred, but not exclusive, electromagnetic beam directing means is a Mooney-type rhomb and that typical sample analysis systems to which the present invention can be applied include reflectometers, ellipsometers and polarimeters.

The present invention provides, however, that in use a sample system be positioned other than on said sample analysis system sample system supporting stage, and that an electromagnetic beam be caused, by said sample analysis system, to interact with said sample system. Said electromagnetic beam is also caused to interact with said electromagnetic beam directing means present in combination with said sample analysis system sample system supporting stage and is, thereby, directed into a sample analysis system detector.

A typical sample analysis system to which the present invention is applied is comprised of a source of an electromagnetic beam, a sample analysis system sample system supporting stage for use in supporting a sample system and a sample analysis system detector. In use said source of an electromagnetic beam, sample analysis system sample system supporting stage for use in supporting a sample system and sample analysis system detector are oriented with respect to one another such that if a sample system is positioned upon said sample analysis system sample system supporting stage, and an electromagnetic beam is caused to interact therewith by said sample analysis system, said electromagnetic beam is then caused to be directed into said sample analysis system detector as a result of said interaction. Typically, analysis of an electromagnetic beam entering a detector involves determination of amplitude change, and/or phase shift between quadrature components effected by interaction with a sample system. As well, ratios of such parameters can also be utilized.

It is further noted that a preferred embodiment of the present invention utilizes an electromagnetic beam which is comprised of more than one wavelength and a plurality of wavelengths can be investigated independently.

The present invention further provides that at least one additional electromagnetic beam directing means, located at a position on said sample analysis system sample system supporting stage, or other than on said sample analysis system stage, can be present.

A method of analyzing a sample system utilizing the present invention involves providing a combination of an electromagnetic beam directing means and a sample analysis system sample system supporting stage for use in supporting a sample system, in a sample system analysis system such as an reflectometer, ellipsometer, or polarimeter. In use, however, a sample system is positioned other than on said sample analysis system sample system supporting stage, such that when an electromagnetic beam is caused to interact with said sample system by said sample analysis system, it is also caused to interact with said electromagnetic beam directing means present on said sample analysis system sample system supporting stage and be, thereby, directed into a sample analysis system detector. Said method of use further comprises providing a sample system at a location removed from said sample analysis system sample system supporting stage; causing an electromagnetic beam to be produced by said sample analysis system and interact with said sample system; and further causing said electromagnetic beam to interact with said electromagnetic beam directing means present in combination with said sample analysis system sample system supporting stage. The end result being that said electromagnetic beam is caused to enter said sample analysis system detector without any change in orientation with respect to said source of an electromagnetic beam and sample analysis system sample system supporting stage; wherein said sample analysis system detector said electromagnetic beam is caused to be subjected to analysis.

A method of use of the present invention can further comprise the steps of: removing said electromagnetic beam directing means from said sample analysis system sample system supporting stage; placing a sample system upon said sample analysis system sample system supporting stage; causing an electromagnetic beam to be produced by said sample analysis system, interact with said sample system and, without any change being effected in the relative orientation of said source of an electromagnetic beam and sample analysis system sample system supporting stage, be directed into said sample analysis system detector; wherein said sample analysis system detector said electromagnetic beam is caused to be subjected to analysis. It is to be understood that said additional steps serve to demonstrate a major advantage of the present invention as compared to sample analysis systems such as reflectometers, ellipsometers and polarimeters, which are not fitted with the present invention system. That is, in reflectometer, ellipsometer and polarimeter and the like sample analysis systems which are not fitted with the present invention system, it is necessary to completely reconfigure the relative orientation of said source of an electromagnetic beam and said sample analysis system detector when said sample analysis system is utilized to investigate sample systems mounted other than on said sample analysis system sample system supporting stage. The present invention system then provides utility by facilitating the ease of use of a reflectometer, ellipsometer, polarimeter and the like sample analysis system in analysis of sample systems mounted alternatingly on, and other than on, said sample analysis system sample system supporting stage. A user can align a reflectometer, ellipsometer, polarimeter or the like sample analysis system for use in investigating sample systems mounted to said sample analysis system sample system supporting stage, and without reconfiguration of the relative positioning of the source of an electromagnetic beam and a sample analysis system detector, investigate sample systems placed other than on said sample analysis system sample system supporting stage. This is accomplished by simply adding the present invention electromagnetic beam directing means to said sample analysis system sample system supporting stage, when sample systems to be analyzed are mounted other than thereon. (It is to be understood that when changing the position of a sample system, it will still be necessary to align the sample system such that the electromagnetic beam is caused to properly enter the sample analysis system detector, whether directly, or via a present electromagnetic beam directing means).

It is further noted that the present invention can further include the use of at least one additional electromagnetic beam directing means located at a position on, or other than on, said sample analysis system sample system supporting stage to aid with directing an electromagnetic beam into the sample analysis system detector.

It is to be noted that an electromagnetic beam directing means can be selected to provide various effects upon a polarized electromagnetic beam caused to interact therewith. For instance, a Mooney-type rhomb can provide, either alone or in combination with other present electromagnetic beam directing means, approximately eighty (80) degrees retardance between quadrature components thereof. This can be useful in converting a linearly polarized beam to an other than linearly polarized, (eg. essentially circularly polarized), electromagnetic beam prior to entry thereof into a sample analysis system detector. This can be important where polarization dependent sensitivity in a sample analysis system detector is a problem. It is also noted, however, that a simple reflective mirror can be utilized to direct an electromagnetic beam, with polarization state being determined by other means in said electromagnetic beam pathway.

The present invention will be better appreciated by reference to the Detailed Description Section of this Disclosure, with appropriate referral to the accompanying Drawings.

SUMMARY OF THE INVENTION

It is therefore a purpose of the present invention system to teach a system which provides utility by facilitating the ease of use of a reflectometer, ellipsometer or polarimeter or the like sample analysis system in analysis of sample systems mounted alternatingly on, and other than on a sample analysis system sample system supporting stage.

It is another purpose of the present invention to teach that utilization of the system thereof allows a user to align a reflectometer, ellipsometer or polarimeter or the like sample analysis system for use in investigating sample systems mounted to said sample analysis system sample system supporting stage, and without reconfiguration, simple add the present invention electromagnetic beam directing means to said sample analysis system sample system supporting stage, when sample systems to be analyzed are mounted other than on said sample analysis system sample system supporting stage.

It is yet another purpose of the present invention to disclose that the system thereof can further include the use of at least one additional electromagnetic beam directing means located at a position on or other than on said sample analysis system sample system supporting stage to aid with directing an electromagnetic beam into the sample analysis system detector.

It is still yet another purpose of the present invention to teach that an electromagnetic beam directing means can be selected to provide various effects upon a polarized electromagnetic beam, such as converting a linearly polarized beam to other than linearly polarized, (eg. essentially circularly polarized), electromagnetic beam prior to entry thereof into a sample analysis system detector, to decrease the effect of polarization dependent sensitivity thereof.

DETAILED DISCLOSURE

Figure 1:
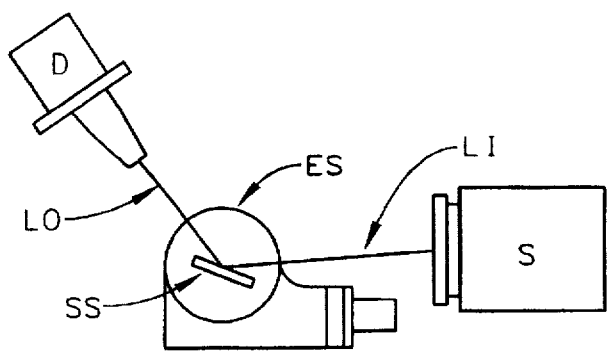
FIG. 1 shows a typical reflectometer, ellipsometer or polarimeter and the like sample analysis system with a sample system mounted upon a sample analysis system sample system supporting stage thereof.

Turning now to the Drawings, there is shown in FIG. 1, a typical reflectometer, ellipsometer or polarimeter system. Shown are a source (S) of an incident electromagnetic beam (LI), a sample analysis system sample system supporting stage (ES), a sample system (SS), a reflected electromagnetic beam (LO) and a sample analysis system detector (D). In use said source (S) of an incident electromagnetic beam (LI), sample analysis system sample system supporting stage (ES) for use in supporting a sample system (SS) and sample analysis system detector (D) are oriented with respect to one another such that if a sample system (SS) is positioned as shown upon said sample system supporting stage (ES), and the incident electromagnetic beam (LI) is caused to interact therewith by said sample analysis system, the reflected electromagnetic beam (LO) is directed into said sample analysis system detector (D) as a result of said interaction.

Figure 2:
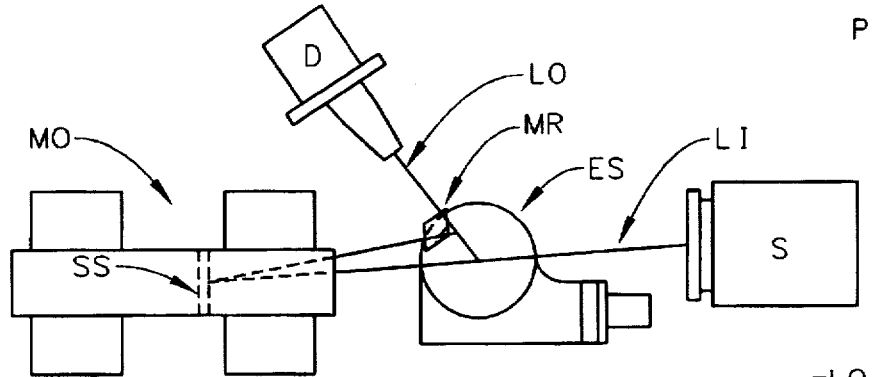
FIG. 2 shows a reflectometer, ellipsometer or polarimeter and the like sample analysis system with a sample system mounted other than upon a sample analysis system sample system supporting stage thereof, with the present invention electromagnetic beam directing means present upon said sample analysis system sample system supporting stage thereof.
Figure 5:
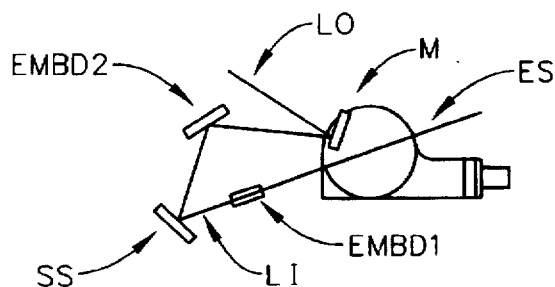
FIG. 5 shows a partial electromagnetic beam path diagram with an additional electromagnetic beam directing means present therein.

Turning now to FIG. 2, it will be appreciated that the present invention is substantially found in a combination of an electromagnetic beam directing means (MR) and a sample analysis system sample system supporting stage (ES) which is typically utilized to supporting a sample system (SS), in a sample system analysis system. It is noted that a preferred electromagnetic beam directing means (MR) is a Mooney-type Rhomb, although, as shown in FIG. 5 a simple Reflective, Non-Retardation entering Element (M), can also be utilized. (It is noted that the Non-Retardation entering Element can be a Mirror, but that some Mirrors can also introduction Retardation). The present invention provides that in use a sample system (SS) be positioned other than on said sample analysis system sample system supporting stage (ES), and an incident electromagnetic beam (LI) be caused, by said sample analysis system, to interact with said sample system (SS). Note that a Magneto-Optic system requires that said incident electromagnetic beam (LI) approaches said sample system (SS) along a locus essentially perpendicular to the sample system (SS) surface. This, however, is not a requirement of the present invention. The present invention requires only that a reflected electromagnetic beam (LO) is caused to interact with said electromagnetic beam directing means (MR), (which is mounted to said sample analysis system sample system supporting stage (ES)) and is, thereby, directed into a sample analysis system detector (D).

FIG. 2 shows the sample system (SS) mounted in a Magneto-Optics system (MO) which requires that a sample system (SS) be located within magnet(s) which are physically too large to be fit upon a sample analysis system sample system supporting stage (ES). It is specifically noted, however, that the present invention is not limited to use with Magneto-Optic magnet systems and is generally applicable in any scenario in which a sample system (SS) is mounted other than on a sample analysis system sample system supporting stage (ES). This can include where a sample system (SS) is simply too large, or where a sample system (SS) is placed in a relatively large heating or cryogenic or radiation producing system, or Molecular-Beam-Epitaxy (MBE) System, or X-Ray system, or particle bombardment system etc.

It is also to be appreciated that the position of the Source (S) of the incident electromagnetic beam (LI), and the sample analysis system detector (D), can be reversed in FIG. 2 and be withing the scope of the present invention. That is, the electromagnetic beam directing means (MR) can be position so that an incident electromagnetic beam encounters said sample system (SS) either before, or after, encountering said electromagnetic beam directing means (MR), in use. In such an arrangement the Source of an electromagnetic beam, in FIG. 2, would be identified by the indicator (D), and the incident electromagnetic beam would be identified as shown as (LO). The sample analysis system Detector would be identified by (S) as shown in FIG. 2, with redirected electromagnetic beam (LI) entering thereto. It is to be understood then that the Claims are to be interpreted to include the physical arrangement where an incident electromagentic beam is redirected prior to interacting with a Sample System per se., and where an electromagnetic beam is redirected after such interaction.

Figure 3:
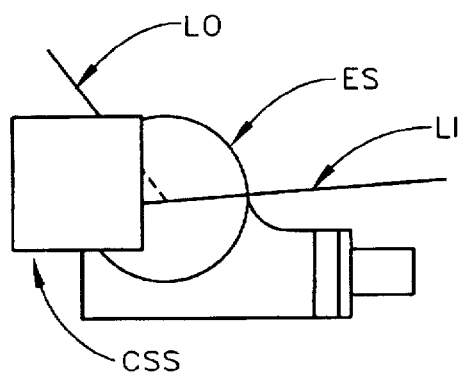
FIG. 3 shows a blown-up top view a reflectometer, ellipsometer or polarimeter and the like present invention sample analysis system sample system supporting stage and a representation of a composite sample system comprised of a sample system per se. and an electromagnetic beam directing means.

FIG. 3 shows a blown-up view of the sample analysis system sample system supporting stage (ES) in combination with a "Black-Box" representation of a Composite Sample System (CSS), which Composite Sample System is comprised of at least one electromagnetic beam directing means and a Sample System per se.

Figure 4:
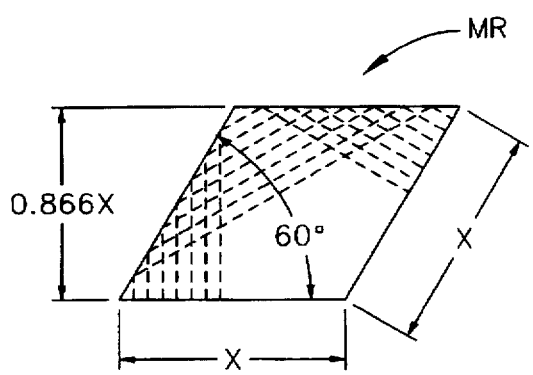
FIG. 4 shows a blown-up top view of a Mooney-type rhomb electromagnetic beam directing means.

FIG. 4 shows a blown-up top view of a Mooney-type rhomb embodiment of an electromagnetic beam directing means, with relative dimensions and an angle between sides indicated. A typically utilized present invention Mooney-type rhomb will have a side "X" dimension of one-and-three-eights (1⅜) inches.

By reference to FIG. 5 it will be further appreciated that the present invention can further include the use of at least one additional electromagnetic beam directing means (EMBD2) located at a position other than on said sample analysis system sample system supporting stage (ES) to aid with directing an electromagnetic beam into the sample analysis system detector (D). This might be utilized where an incident electromagnetic beam (LI) is applied other than along a locus essentially perpendicular to a surface of a sample system (SS), for instance. As well, said at least one additional electromagnetic beam directing means (EMBD2) could be located upon said sample analysis system sample system supporting stage (ES). It is further noted that the electromagnetic beam directing means (EMBD2) can be a means for effecting a change in polarization state, such as, for instance, a Retarder which serves to impose a retardation on a component of an electromagnetic beam caused to interact therewith. Note that Retardation could be entered in an electromagnetic beam prior to the Sample System (SS), by an element identified as (EMBD1), as well as, or instead of, thereafter. It is noted that said Retarder can be variable, such that, for instance, rotation and/or tilting thereof changes the amount of retardation entered to an electromagnetic beam caused to interact therewith. Berek-type Retarders, which have their Optical Axis perpendicular to the surface thereof being particularly applicable. As well, note that the Mooney-type Rhomb (MR) shown in FIG. 2, in combination with a sample analysis system sample system supporting stage is shown as replaced by a Mirror (M) in FIG. 5. Where this embodiment is utilized, any Retardation effects can be predominantly imposed by elements such as electromagnetic beam directing means (EMBD1) and/or (EMBD2). It is also noted that a Retardation effecting element can be placed so as to interact with the electromagnetic beam directly after it interacts with the Sample System (SS), and/or after it reflects from the Mirror (M). That is, there are no implied limitations on positioning of such Retardation effecting elements as long as they are positioned to interact with the electromagnetic beam pathway.

It is emphasized that a Mooney-type Rhomb (MR) electromagnetic beam directing means can be selected to provide various effects upon a polarized electromagnetic beam caused to interact therewith. For instance, a Mooney-type rhomb can provide, either alone or in combination with other present electromagnetic beam directing means (ie. (EMBD1) and/or (EMBD2)), approximately eighty (80) degrees retardance between electric field quadrature components of a Polarized electromagnetic beam. This can be useful in converting a linearly polarized beam to an essentially circularly polarized electromagnetic beam prior to entry thereof into a sample analysis system detector. This can be important where polarization dependent sensitivity in a detector is a problem. As well, it is to be noted that a Mooney-type rhomb can be used to provide an intended number of degrees retardance, and any other electromagnetic beam directing means (EMBR) can be designed to a total of provide one-hundred-eighty (180) or three-hundred-sixty (360) degrees retardance, thereby appearing to provide essentially no retardance as monitored by a Detector (D).

A method of analyzing a sample system (SS) utilizing the present invention is described in the Disclosure of the Invention Section of this Disclosure, however, it is again noted that a major advantage of the present invention as compared to sample analysis systems such as ellipsometers and polarimeters, which are not fitted with the present invention system, is that in reflectometer, ellipsometer and polarimeter and the like sample analysis systems which are not fitted with the present invention system, it is necessary to completely reconfigure the relative orientation of said source (S) of an incident electromagnetic beam (LI), and said sample analysis system detector (D) when said sample analysis system is utilized to investigate sample systems (SS) mounted other than on said sample analysis system sample system supporting stage (ES), (see FIG. 2). The present invention system then provides utility by facilitating the ease of use of a reflectometer, ellipsometer, polarimeter and the like sample analysis system in analysis of sample systems (SS) mounted on, and other than on, said sample analysis system sample system supporting stage (ES). A user can align a reflectometer, ellipsometer or polarimeter or the like sample analysis system for use in investigating sample systems (SS) mounted to said sample analysis system sample system supporting stage (ES), and without reconfiguration, simple add the present invention electromagnetic beam directing means (MR) to said sample analysis system sample system supporting stage (ES), when sample systems (SS) to be analyzed are mounted other than thereon, (see FIG. 2). To again use the reflectometer, ellipsometer or polarimeter or the like sample analysis system for use in investigating sample systems (SS) mounted to said sample analysis system sample system supporting stage (ES) it is only necessary to remove the present invention electromagnetic beam directing means (MR) and place a sample system (SS) upon said sample analysis system sample system supporting stage (ES), (see FIG. 1). (It is to be noted that Sample System (SS) alignment will still be necessary, but relative alignment between a source (S) of electromagnetic beam and a sample analysis system detector (D) becomes unnecessary).

With the foregoing in mind, it is noted that the present invention can be considered as a means for providing an "Effective Sample System" comprised of a Sample System (SS) per se. and an electromagnetic beam directing means (MR), which Effective Sample System causes an electromagnetic beam entered thereto by a source of electromagnetic beam, to enter a sample analysis system detector.

It is noted that the terminology "electromagnetic beam directing means (MR)" is to be interpreted broadly to include any means for directing an electromagnetic beam, such as, but not limited to, a Mooney Rhomb, a Non-Retardation entering Reflective Element, a Retardation entering Reflective or Transmitting Element, a Prism etc.

It is further noted that a preferred embodiment of the present invention utilizes an incident electromagnetic beam (LI) which is comprised of more than one wavelength.

Having hereby disclosed the subject matter of the present invention, it should be obvious that many modifications, substitutions, and variations thereof are possible in light thereof. It is therefore to be understood that the present invention can be practiced other than as specifically described, and should be limited in breadth and scope only by the claims.

We claim:

1. A sample analysis system which utilizes an electromagnetic beam to measure characterizing parameters of a sample system, said sample analysis system comprising a combination of an electromagnetic beam directing means and a sample analysis system sample system supporting stage, usage of which sample analysis system allows measurement of characterizing parameters of a sample system positioned other than on said sample analysis system sample system supporting stage; such that in use an electromagnetic beam provided by a source of an electromagnetic beam, is caused by said sample analysis system to interact with said sample system, and with said electromagnetic beam directing means, and thereby be directed into a sample analysis system detector.

2. A sample analysis system with a sample system positioned as in claim 1; wherein said source of an electromagnetic beam, said sample system supporting stage and said sample analysis system detector are oriented with respect to one another such that if said electromagnetic beam directing means is removed from combination with said sample analysis system sample system supporting stage and a sample system is positioned upon said sample analysis system sample system supporting stage, and an electromagnetic beam provided by said source of an electromagnetic beam is caused to interact with said sample system by said sample analysis system, said electromagnetic beam is directed into said sample analysis system detector without any change being required in the relative orientation of said source of an electromagnetic beam and sample analysis system sample system detector.

3. A sample analysis system as in claim 1; wherein said electromagnetic beam directing means is a selection from the group consisting of: (a retardation entering element and a non-retardation entering element).

4. A sample analysis system as in claim 3, wherein said electromagnetic beam directing means provides retardance to a component of a polarized electromagnetic beam caused to interact therewith and is a Mooney-type rhomb.

5. A sample analysis system as in claim 1, wherein said electromagnetic beam which is comprised of more than one wavelength.

6. A sample analysis system as in claim 1, wherein at least one additional electromagnetic beam directing means is present and is located at a position selected from the group consisting of: (on said sample analysis system sample system supporting stage and other than on said sample analysis system sample system supporting stage).

7. A sample analysis system as in claim 6, wherein said at least one additional electromagnetic beam directing means is a selection from the group consisting of: (a retardation entering element and a non-retardation entering element).

8. A sample analysis system as in claim 1, which is a selection from the group consisting of: (reflectometer, ellipsometer and polarimeter) systems.

9. A method of analyzing a sample system comprising the steps of:

a. providing a sample analysis system which utilizes an electromagnetic beam to measure characterizing parameters of a sample system, said sample analysis system comprising a combination of an electromagnetic beam directing means and a sample analysis system sample system supporting stage, usage of which sample analysis system allows measurement of characterizing parameters of a sample system positioned other than on said sample analysis system sample system supporting stage; such that in use an electromagnetic beam provided by a source of an electromagnetic beam is caused, by said sample analysis system, to interact with said sample system, and with said electromagnetic beam directing means, and thereby be directed into a sample analysis system detector;

wherein said source of an electromagnetic beam, said sample system supporting stage and said sample analysis system detector are oriented with respect to one another such that if said electromagnetic beam directing means is removed from combination with said sample analysis system sample system supporting stage and a sample system is positioned upon said sample analysis system sample system supporting stage, and an electromagnetic beam provided by said source of an electromagnetic beam is caused to interact with said sample system by said sample analysis system, said electromagnetic beam is directed into said sample analysis system detector without any change being required in the relative orientation of said source of an electromagnetic beam and sample analysis system sample system detector;

b. providing a sample system, characteristic parameters of which are to be measured, said sample system being present at a location removed from said sample analysis system sample system supporting stage;

c. causing an electromagnetic beam to be provided by said source of an electromagnetic beam and interact, in a functional order, with said sample system and with said electromagnetic beam directing means which is present in combination with said sample analysis system sample system supporting stage;

the result being that said electromagnetic beam is caused to enter said sample analysis system detector without any change in relative orientation between said source of an electromagnetic beam and sample analysis system detector, as described in step a., being required, and in which sample analysis system detector said electromagnetic beam is caused to be subjected to analysis.

10. A method of analyzing a sample system as in claim 9 which further comprises the steps of:

d. placing a sample system upon said sample analysis system sample system supporting stage;

e. causing an electromagnetic beam to be produced by said source of an electromagnetic beam and interact with said sample system, and without any change being effected in the relative orientation of said source of an electromagnetic beam and sample analysis system sample system detector as described in step a., be directed into said sample analysis system detector;

wherein said sample analysis system detector said electromagnetic beam is caused to be subjected to analysis.

11. A method of analyzing a sample system as in claim 9 which further comprises the steps of causing said electromagnetic beam to further interact with at least one additional electromagnetic beam directing means located at a position selected from the group consisting of: (on said sample analysis system sample system supporting stage and other than on said sample analysis system sample system supporting stage).

* * * * *